United States Patent [19]

Thiem et al.

[11] Patent Number: 5,264,352
[45] Date of Patent: Nov. 23, 1993

[54] PROCESS FOR THE ENZYMATIC SYNTHESIS OF 2-DEOXY-β-D-GALACTOSIDES

[75] Inventors: Joachim Thiem; Torsten Wiemann, both of Hamburg, Fed. Rep. of Germany

[73] Assignee: Hoechst Aktiengesellschaft, Frankfurt am Main, Fed. Rep. of Germany

[21] Appl. No.: 864,800

[22] Filed: Apr. 7, 1992

[30] Foreign Application Priority Data

Apr. 9, 1991 [DE] Fed. Rep. of Germany ....... 4111362

[51] Int. Cl.$^5$ .................... C12P 19/18; C12P 19/12; C12P 19/28; C12N 9/10
[52] U.S. Cl. ..................................... 435/97; 435/74; 435/75; 435/84; 435/85; 435/100; 435/193
[58] Field of Search ...................... 435/84, 97, 100, 74, 435/75, 85, 193

[56] References Cited

FOREIGN PATENT DOCUMENTS

0414171A2 2/1991 European Pat. Off. .
3927801 2/1991 Fed. Rep. of Germany .

OTHER PUBLICATIONS

Joachim Thiem et al., "Galactosyltransferase-catalyzed synthesis of 2'-N-acetyllactosamine", Angewandte Chemie. International Edition. 1-8 Bd. 30 No. 9, 1163-1164 Sep. 1991.
Advances In Carbohydrate Chemistry, vol. 17 (1962), pp. 65-121, by T. Reichstein and E. Weiss.
Topics In Current Chemistry, 154 (1990), pp. 284-333 by J. Thiem and W. Klaffke.
Molecular and Cellular Biochemistry, vol. 62 (1984), pp. 37-42 by L. Berliner, M. Davis, K. Ebner, T. Beyer & J. Bell.
The Journal Of Organic Chemistry, vol. 47 (1982), pp. 5416-5418 by S. Haynie, C. Wong, G. Whitesides.
Pure And Applied Chemistry, vol. 59, No. 11, (1987) pp. 1501-1508 by S. David and C. Augé.
Dechema Biotechnology Conferences, Ed.: D. Behrens, Verlag Chemie, Weinheim, vol. 2, (1988), pp. 189-204 by J. Thiem, W. Treder, T. Wiemann.
Angewandte Chemie, 102(1990)1, pp. 78-80 by J. Thiem and T. Wiemann.
Biochemistry, vol. 21, No. 25 (1982) pp. 6340-6343 by L. Berliner and R. Robinson.
Carbohydrate Research, vol. 19, (Aug. 1971) No. 1, pp. 231-241 by D. Cowley, L. Hough and C. Peach.
The Journal of Biological Chemistry, vol. 245, (1970) No. 16, pp. 4158-4162 by M. Spinola and R. Jeanloz.
Angewandte Chemie, 97(1985), pp. 885-887 by H. Kunz and H. Waldmann.
Annual Review of Biochemistry, vol. 57, (1988) pp. 785-838 by T. Rademacher, R. Parekh, and R. Dwek.
Edelman, Spektrum Wiss. 1984(6), pp. 62-74.
Ginsburg, Adv. Enzymol. 36, (1972), pp. 131-149, Enzymatic Basis For Blood Groups In Man.
Cook et al., Surface Carbohydrates of the Eukaryotic Cell, Academic Press, London 1973, pp. 257-270.
Albersheim et al., Spektrum Wiss. 1985 (11), pp. 86-93.
Palcic et al., "Flexibility in the Donor Substrate Specificity of β1, 4-Galactosyltransferase: Application in the Synthesis of Complex Carbohydrates," Glycobiology vol. 1, No. 2, pp. 205-209 (1991).

*Primary Examiner*—Herbert J. Lilling
*Attorney, Agent, or Firm*—Finnegan, Henderson, Farabow, Garrett & Dunner

[57] ABSTRACT

The invention relates to a process for the enzymatic synthesis of 2-deoxy-β-D-galactosides. The enzyme galactosyltransferase is able to catalyze the transfer of 2-deoxygalactose residues from the donor substrate uridine 5'-diphospho-2-deoxy-D-galactose to N-acetylglucosamine or aspartyl-N-acetylglucosamine or, in the presence of lactose, to terminal glucose.

8 Claims, No Drawings

PROCESS FOR THE ENZYMATIC SYNTHESIS OF 2-DEOXY-β-D-GALACTOSIDES

DESCRIPTION

Many complex carbohydrates play a central part in biological recognition processes [G. E. Edelman, Spektrum Wiss. 1984 (6), 62], such as, for example, cell-cell recognition, cell growth and cell differentiation. They constitute the blood-group determinants [V. Ginsburg,, Adv. Enzymol. 36, (1972), 131] and form tumor-associated antigens [G. M. W. Cook, E. W. Stoddart, "Surface Carbohydrates of the Eucaryotic Cell", Academic Press, London 1973]. In the plant kingdom they may exert regulatory function as hormones [P. Albersheim, A. G. Darvill, Spektrum Wiss. 1985 (11), 86] and form the binding site for lectins [T. W. Rademacher, R. B. Parekh, R. A. Dwek, Ann. Rev. Biochem, 57, (1988), 785].

Modified sugars such as, for example, deoxy- and fluoro-sugars, and the epimers of natural sugars represent important tools for research into these interactions. The general rules of protein-carbohydrate interaction are just as much the center of interest in this connection as specific enzyme-substrate interactions. Thus, for example, information about the active center of enzymes can be obtained by successive modification of enzyme substrates. Furthermore, there is particular interest precisely in deoxyglycosides owing to their occurrence in many antibiotics [T. Reichstein, E. Weiss, Adv. Carbohydr. Chem. 17, (9162 [sic]), 65].

Specific chemical syntheses of 2-deoxyglycosides are extremely difficult owing to the absence of a directing effect of a substituent in position 2 and, without long synthetic sequences, as a rule α/β mixtures are obtained [J. Thiem, W. Klaffke, Top. Curr. Chem. 154, (1990), 285]. In addition, elaborate protective group chemistry is often necessary in such syntheses, and this entails a corresponding increase in the number of stages and a reduction in the yield.

In recent years, the preparative utilization of enzymes has been increasingly used in sugar chemistry. High stereo- and regioselectivity with, at the same time, avoidance of protective group chemistry ensures that the yield is good compared with chemical synthesis.

The term 'preparative utilization' is defined as follows: enzymes of high substrate specificity ensure, on the one hand, that no interfering side reactions occur and, on the other, that there is little or no inhibition by product or substrate during the enzymatic reaction, so that the reaction product can be obtained in milligram or gram quantities.

The galactosyltransferase EC 2.4.1.22 transfers galactose residues regio- and stereospecifically to terminal N-acetylglucosamine units, also to terminal glucose in the presence of α-lactalbumin, with formation of a β-(1-4) glycosidic linkage.

The specificity of the transferase allows a relatively wide scope in terms of variation in the acceptor substrate [L. J. Berliner, M. E. Davis, K. E. Ebner, T. A. Beyer, J. E. Bell, Mol. Cell. Biochem. 62, (1984), 37] and it has already been possible in some cases to make preparative use of this scope [S. L. Haynie, C.-H. Wong, G. M. Whitesides,, J. Org. Chem., 47, (1982), 5416; S. David, C. Auge, Pure Appl. Chem. 59, (1987), 1501; J. Thiem, W. Treder, T. Wiemann, Dechema Biotechnology Conferences, Ed.: D. Behrens, Verlag Chemie, Weinheim, Vol. 2, (1988), 189; J. Thiem, T. Wiemann, Angew. Chem., 102, (1990), 78].

There are distinct limitations on variation of the donor substrate, in contrast to the acceptor substrate. Apart from the natural substrate, the only other compound recognized by the transferase is UDP-4"-deoxyglucose (Berliner and Robinson, Biochemistry 1982, 21, p. 6340). Berliner and Robinson detect the resulting reaction product only by thin layer chromatography. There are no statements about the occurrence of interfering side reactions or the formation of products of side reactions, because the quantities of substrate and enzyme employed for this are probably too small.

A process for the enzymatic synthesis of galactosylated glycoprotein building blocks is described in European Patent Application 90 11 5862.6 and in this the galactosyltransferase also allows the synthesis of glycoasparagines.

It has now been found that the galactosyltransferase is, surprisingly, also able to transfer 2-deoxy-D-galactose residues and accepts them in the form of the uridine 5'-diphospho-2-deoxy-D-galactose of the formula II as donor substrate.

The invention thus relates to a process for the preparative synthesis of the compound of the formula I

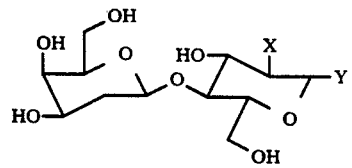

in which X is OH or NH-acetyl and Y is OH or

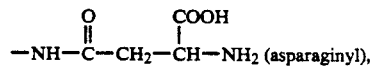

which comprises reacting the compound of the formula II

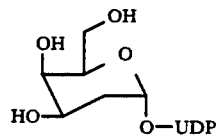

with the compound of the formula III

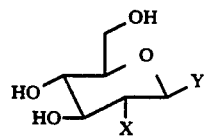

in which the substituent X is OH or —NH—Ac and Y is OH or

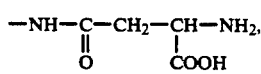

in the presence of the enzyme galactosyltransferase, the reaction being carried out with the aid of the coenzyme lactalbumin to give lactose when the substituent X is a hydroxyl group.

The invention is described in its preferred embodiments in detail hereinafter. The invention is furthermore defined by the contents of the claims.

Galactosyltransferase EC 2.4.1.22, also called lactose is synthetase, accepts uridine 5'-diphospho-2-deoxy-D-galactose (UDP-2D-Gal) of the formula II as donor substrate in order to transfer 2-deoxygalactose in β(1,4) glycosidic linkage to terminal N-acetylglucosamine, aspartyl-N-acetylglucosamine or glucose residues.

The process according to the invention can be started in a so-called "one-pot process". By a one-pot process is meant that all substrates involved and all enzymes involved are put together in one reaction mixture. It is also, of course, possible for the reactions specified hereinafter to be carried out successively. However, a one-pot process proved to be more economic when the reactants described above are maintained for the complete mixture.

UDP-2D-Gal (II) is advantageously prepared in situ from 2-deoxyglucose 6-phosphate: 2-deoxyglucose 6-phosphate is isomerised by the phosphoglucomutase EC 2.7.5.1 to 2-deoxyglucose 1-phosphate. 2-deoxyglucose 1-phosphate is reacted with uridine 5'-triphosphate (UTP) in the presence of uridine-5'-diphosphoglucose pyrophosphorylase EC 2.7.7.9 to give uridine 5'-diphospho-2-deoxyglucose. Hydrolysis of the pyrophosphate with inorganic pyrophosphatase EC 3.6.1.1 shifts the reaction catalysed by uridine-5'-diphosphoglucose pyrophosphorylase in the direction of the required products. Uridine 5'-diphospho-2-deoxyglucose is epimerized by uridine-51-diphosphogalactose 4-epimerase, EC 5.1.3.2 to UDP-2D-Gal of the formula II which can undergo the transfer reaction to N-acetylglucosamine or, in the presence of α-lactalbumin, to glucose.

The uridine 5'-diphosphate (UDP) formed in this reaction is preferably phosphorylated to UTP by catalysis with pyruvate kinase EC 2.7.1.40. Phosphoenolpyruvate (PEP) is used as phosphate donor. The UTP can again undergo the reaction forming the nucleotide-sugar uridine 5'-diphospho-2-deoxyglucose. Since the cofactor UTP is continuously regenerated, it needs to be employed only in catalytic amounts.

The reaction sequence is preferably carried out using carriers based on modified carbohydrates, such as, for example, with enzymes immobilized on activated CH-®Sepharose 4B [Affinity Chromatography, Principles and Methods, Pharmacia]. The immobilization makes it possible to recover [sic] the enzymes in further reaction mixtures.

Tris buffer (100 mM, pH 7.0-8.0, preferably pH 7.5) is used as reaction medium. The mixture is incubated at 28°-35° C., preferably 300° C., for 5–10 days, preferably 7 and the product is subsequently isolated by chromatography on gel ion exchangers (styrene/divinylbenzene copolymers, degree of crosslinking 8%), for example ®Dowex 1×8 (counter ion: Cl⁻) and then on porous, hydrophilic and completely charge-free polyacrylamide gels, for example ®Bio-Gel P2. The yield is 35–40%. The 2-deoxyglucose 6-phosphate used as starting material for the reaction described above is previously prepared from 2-deoxyglucose. This reaction is catalysed by hexokinase EC 3.6.1.1 and requires adenosine 51-triphosphate (ATP) as cofactor. The adenosine 5'-diphosphate (ADP) which is formed is phosphorylated, in analogy to the regeneration of UTP described above, with phosphoenolpyruvate (PEP) in the presence of pyruvate kinase. The hexokinase and the pyruvate kinase are preferably immobilized on spherical, macroporous bead polymers of vinyl acetate and dimethyleneurea which have been modified with oxirane groups, such as, for example, VA-Epoxy (Riedel-de Haen).

Unless otherwise described, all the starting compounds such as, for example, the enzyme galactosyltransferase or the compounds of the formula III can be obtained commercially or can be chemically synthesized based on papers by various authors [D. E. Cowley, L. Hough, C. N. Peach, Carbohydr. Res. 19 (1971) 231; M. Spinola, R. W. Jeanloz, J. Biol. Chem. 245 (1970) 4158; E. Kunz, B. Waldmann, Angew. Chem. 97 (1985) 885]. If aspartyl-N-acetylglucosamine is employed as acceptor substrate, the reaction is carried out as described in European Patent Application 90 11 5862.1.

The progress of the reaction is detected by thin-layer chromatography. The final product is isolated, after removal of the nucelotide [sic] phosphates, by ion exchange chromatography, such as, for example, on Dowex 1×8 (counter ion: Cl⁻) and gel chromatography with, for example, Bio-Gel P2 ®, giving a yield of 25–35%. The ion exchange chromatography is thus a step in the isolation of the final product and in the removal of UDP. Since the enzyme used catalyzes the reaction very specifically, there are no products of side reactions which need to be removed. The final product can be eliminated by gel permeation chromatography on Bio-Gel P2 ®.

The invention is explained further with the aid of examples hereinafter.

EXAMPLES

1) Synthesis of 2-deoxy-D-glucopyranosyl 1-phosphate (2)

1.1) Immobilization of hexokinase (I) and pyruvate kinase (II) on VA-Epoxy.

| Immobilization buffer for I: | HEPES | 300 mM | pH 7.5 |
|---|---|---|---|
| | glucose | 25 mM | |
| | ADP | 10 mM | |
| Immobilization buffer for II: | HEPES | 300 mM | pH 7.5 |
| | MgCl₂ | 30 mM | |
| | ADP | 10 mM | |

Oxygen is removed from the buffer by passing in nitrogen. 0.5 g portions of VA-Epoxy are suspended in the particular buffer, and then vacuum is cautiously applied in order to fill the pores of the carrier with liquid. Hexokinase (1000 U) and pyruvate kinase (1000 U) are added and the mixture is left on a shaker for 2 days. The immobilized enzymes are ready for use after filtration and washing.

Activity yield: 70–80%.

1.2) 2-Deoxy-D-glucopyranosyl 1-phosphate (2)

2-Deoxyglucose (1, 395 mg, 2.4 mmol), phosphoenolpyruvate (536 mg, 2.6 mmol), magnesium chloride (95 mg, 24 mmol), potassium chloride (300 mg, 100 mmol) and adenosine triphosphate (12 mg, 20 μmol) are dissolved in 40 ml of deoxygenated water and the pH is adjusted to 7.5. The hexokinase and pyruvate kinase immobilized on VA-Epoxy are added and the mixture is then left on a shaker. After 4 days, precursor is no longer detectable by thin-layer chromatography.

| TLC check: | n-propanol/ethanol/water | 5:3:2 |
|---|---|---|
| | $R_f(1)$: 0.65 | |
| | $R_f(2)$: 0.33 | |

2 is isolated by chromatography on a DEAE-cellulose column (3×30 cm) which has previously been equilibrated with a 30 Mm ammonium bicarbonate solution. After washing with 200 ml of water, the product is eluted with an ammonium bicarbonate gradient (0–0.2M) at a flow rate of 2 ml/min and with a total volume of 2 l. The product-containing fractions (2 elutes at about 30 mM $NH_4HCO_3$) are combined and lyophilized several times in order to remove the ammonium bicarbonate. Yield: 80%.

Preparation of
2-acetamido-2-deoxy-4-O-(2-deoxy-β-D-lyxohexopyranosyl)-D-glucopyranose

| Incubation buffer: | tris | 100 mM | pH 7.5 |
|---|---|---|---|
| | $MnCl_2$ | 5 mM | |
| | $MgCl_2$ | 10 mM | |
| | KCl | 30 mM | |
| | $NaN_3$ | 0.02% | |

2-Deoxyglucose 6-phosphate (2, 60 mg, 190 μmol), N-acetylglucosamine (6, 71 mg, 321 μmol), UDP (2 mg, 5 μmol), PEP (44 mg, 210 μmol), glucose 1, 6-diphosphate (0.1 mg) and bovine serum albumin (BSA, 5 mg) are dissolved in 10 ml of deoxygenated buffer. The enzymes are subsequently added:

| Phosphoglucomutase | 50 U |
|---|---|
| UDP-glucose pyrophosphorylase | 10 U |
| Inorganic pyrophosphatase | 30 U |
| UDP-galactose 4-epimerase | 5 U |
| galactosyltransferase | 1 U |
| pyruvate kinase | 100 U | and the mixture is incubated at 30° C. for 7 d.

| TLC check: | n-propanol/acetic acid/water | 85:12:3 |
|---|---|---|
| | $R_f$(N-acetylglucosamine): 0.50 | |
| | $R_f$(2-deoxyglucose): 0.68 | |
| | $R_f$(2'-deoxylactosamine): 0.32 | |

The conversion can be quantified either by phosphate determination by a modification of Fiske-Subbarow method [T. G. Cooper, "Biochemische Arbeitsmethoden", Walter de Gruyter, Berlin 1981, 53] or by enzymatic determination of pyruvate [R. Czok, W. Lamprecht, "Methoden der enzymatischen Analyse", Ed.: H. U. Bergmeyer, Verlag Chemie, Weinheim, 1974, Vol. 2, 2nd ed., 1491].

The working-up is carried out by removing the anionic constituents with anion exchanger (Dowex 1×8, Cl−form) and subsequent gel chromatography on Bio-Gel P2. Freeze-drying of the product-containing fractions results in the final product being a hygroscopic white substance with a melting point of 136° C. It is not possible to obtain a satisfactory elemental analysis because of the indeterminate water content. Azeotropic drying (taking up in absol. methanol and concentration several times with absol. benzene) results in analytically pure substance.

Yield: 40% (19 mg).

$^1$H-NMR (250 MHz, $D_2O$): δ=5.26 (d, 1H, H-1, α-form), 2.18 (m, 1H, H-2'e), 2.09 (s, 3H, NHAc), 1.76 ppm (m, 1H, H-2'a).

The signals of H-1 (β form) and H-1' are covered by the HDO signal.

$^{13}$C-NMR (63 MHz, $H_2O$ internal standard: dioxane): δ=173.31 ($NH-CO-CH_3$), 99.42 (C-1'), 93.93 (C-1, β-form), 89.59 (C-1, α-form), 77.87 (C-4, α-form), 77.44 (C-4, β-form), 74.65 (C-5'), 73.79 (C-5, β-form), 71.48 (C-3, β-form), 69.17 (C-5, α-form), 68.30 (C-3, α-form), 66.72 (C-3'), 65.73 (C-4'), 60.43 (C-6'), 59.18 (C-6), 55.29 (C-2, β-form), 52.80 (C-2, α-form), 32.54 (C-2'), 21.25 ($NHCO-CH_3$, β-form), 20.97 ppm ($NHCO-CH_3$, α-form).

$C_{14}H_{25}NO_{10}$ (367.35).

FAB-MS: M+1 368. M+Na 390.

Synthesis of 2'-deoxylactose

Tris buffer (100 Mm, pH 7.5) is used as reaction medium. 50 mg of 2-deoxyglucose 6-phosphate (1, 158 μmol, disodium salt sesquihydrate), 6 mg of uridine triphosphate (10 μmol, trisodium salt dehydrate), 36 mg of phosphoenolpyruvate (PEP, 175 μmol, potassium salt) and 43 mg of glucose (5, 235 μmol) are dissolved in 4 ml of the buffer. After the pH has been checked, 4 mg of manganese chloride (20 μmol), 8 mg of magnesium chloride (40 μmol), 11 mg of potassium chloride (148 μmol) and a minute amount of sodium azide are added. Deoxygenation is then carried out by passing in helium. Finally the proteins are added: 2 mg of α-lactalbumin, 4 mg of bovine serum albumin (BSA), 100 U of phosphoglucomutase (I), 10 U of UDP-glucose pyrophosphorylase (II), 50 U of inorganic pyrophosphatase (III), 10 U of UDP-galactose 4-epimerase (IV), 5 U of galactosyltransferase (V) and 100 U of pyruvate kinase (VI). The mixture is incubated at 37° C., if possible in a shaking water bath.

| TLC check: | 60 F254 TLC aluminum sheet (Merck) | 85:12:3 |
|---|---|---|
| | mobile phase: n-propanol/acetic acid/water in the ratio | |
| | Rf(glucose, 5): 0.41 | |
| | Rf(2'-deoxylactose, 6): 0.27 | |
| | Rf(2-deoxy-Glc 6-phosphate, 1): 0.05 | |
| | Rf(2-deoxy-Glc): 0.57 (from hydrol. of 2) | |

Product formation is detectable after one to two days. Half the amounts indicated above of uridine triphosphate and of the enzymes are added once again. After a further two days the mixture is worked up by removing the phosphate esters on an anion exchange column (Dowex 1-×8, 200–400 mesh, counter ion: Cl−, 2.7×20 cm). The eluate (2-deoxyglucose, glucose and 2'-deoxylactose) is lyophilized and then fractionated by gel permeation chromatography (Bio-Gel P2, 2×20 cm).

Yield: 17 mg (33%).

We claim:

1. A process for the preparative synthesis of the compound of the formula I

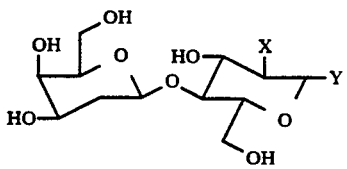

in which X is OH or NH—Ac and Y is OH or

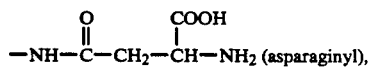

which comprises reacting the Compound of the formula II

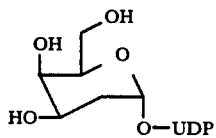

wherein UDP is uridine 5'-diphosphate with the compound of the formula III

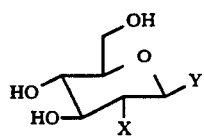

in which the substituent X is OH or —NH—Ac and Y is OH or

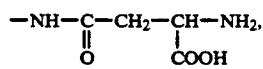

in the presence of the enzyme galactosyltransferase, the reaction being carried out with the aid of the coenzyme lactalbumin to give 2'-deoxylactose when the substituent X is a hydroxyl group.

2. The process as claimed in claim 1, wherein the compound of the formula II is prepared in situ from 2-deoxyglucose 6-phosphate, and the pyruvate kinase EC 2.7.1.40 required for its synthesis is in immobilized form.

3. The process as claimed in claim 2, wherein the hexokinase EC 3.6.1.1 used for the synthesis of 2-deoxyglucose 6-phosphate is employed in immobilized form.

4. The process as claimed in claim 2 wherein the carrier for the immobilizate is a spherical, macroporous bead polymer of vinyl acetate and dimethylethyleneurea, modified with oxirane groups.

5. The process as claimed in claim 1, wherein all substrates involved and all enzymes involved are put together in one reaction mixture.

6. The process as claimed in claim 1, wherein the reaction medium has a pH of 7–8.

7. The process as claimed in claim 1, wherein the reaction temperature is 28°–35° C.

8. The process as claimed in claim 1, wherein the reaction lasts 5–10 days.

* * * * *